(12) United States Patent
Watanabe et al.

(10) Patent No.: US 8,366,606 B2
(45) Date of Patent: Feb. 5, 2013

(54) ENDOSCOPE AND METHOD FOR INSERTING ENDOSCOPE INTO COLON

(75) Inventors: Atsushi Watanabe, Hino (JP); Hiroki Moriyama, Akishima (JP); Takahiro Kishi, Yokohama (JP); Yasuhito Kura, Hachioji (JP); Ryuhei Fujimoto, Tokyo (JP); Katsutaka Adachi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1460 days.

(21) Appl. No.: 11/507,424

(22) Filed: Aug. 21, 2006

(65) Prior Publication Data

US 2007/0043261 A1 Feb. 22, 2007

(30) Foreign Application Priority Data

Aug. 22, 2005 (JP) .................. 2005-240288

(51) Int. Cl.
*A61B 1/00* (2006.01)
(52) U.S. Cl. .................. 600/144; 600/104; 600/114
(58) Field of Classification Search .................. 600/104, 600/114–116, 127, 106, 107, 139–144, 146–152; 604/525–528
See application file for complete search history.

(56) References Cited

U.S. PATENT DOCUMENTS

| | | | |
|---|---|---|---|
| 4,351,323 A * | 9/1982 | Ouchi et al. ............. | 600/142 |
| 5,163,950 A | 11/1992 | Pinchuk et al. | |
| 5,482,029 A | 1/1996 | Sekiguchi et al. | |
| 5,885,208 A | 3/1999 | Moriyama | |
| 5,897,536 A * | 4/1999 | Nap et al. .................. | 604/524 |
| 6,800,056 B2 * | 10/2004 | Tartaglia et al. ............. | 600/114 |
| 2002/0002323 A1 | 1/2002 | Moriyama | |
| 2002/0045852 A1* | 4/2002 | Saab .................. | 604/96.01 |
| 2002/0120178 A1* | 8/2002 | Tartaglia et al. ............. | 600/114 |
| 2004/0054322 A1* | 3/2004 | Vargas .................. | 604/95.04 |
| 2004/0093044 A1 | 5/2004 | Rychnovsky et al. | |
| 2004/0186349 A1* | 9/2004 | Ewers et al. .................. | 600/114 |
| 2005/0131343 A1* | 6/2005 | Abrams et al. ............. | 604/95.04 |

FOREIGN PATENT DOCUMENTS

| | | | |
|---|---|---|---|
| JP | 1-22641 | | 7/1989 |
| JP | 2000-143084 | | 5/2000 |
| JP | 2002-143084 A | | 5/2002 |
| JP | 2002330924 A | * | 11/2002 |
| JP | 2003010106 A | * | 1/2003 |

OTHER PUBLICATIONS

European Office Action dated Apr. 19, 2012 issued in counterpart European Patent Application No. 06017052.9.

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

A first bendable section which can be bent in an arbitrary direction and a second bendable section which can be bent in the bending direction of this first bendable section are provided at the tip end side of an insertion portion. A balloon which is inflated/contracted by feed/discharge of a fluid is provided in this second bendable section so that hardness of this second bendable section can be varied and insertion work into a curved portion is facilitated.

7 Claims, 13 Drawing Sheets

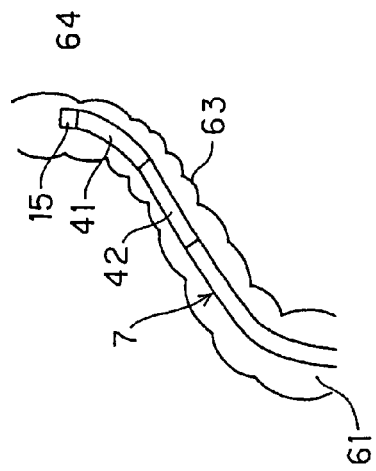
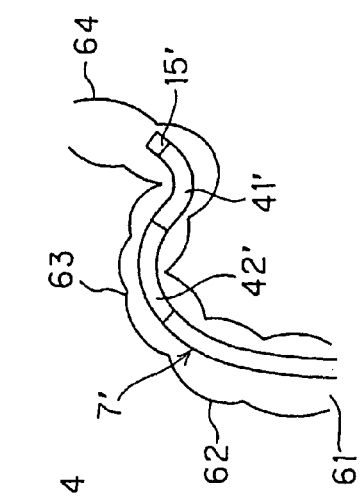
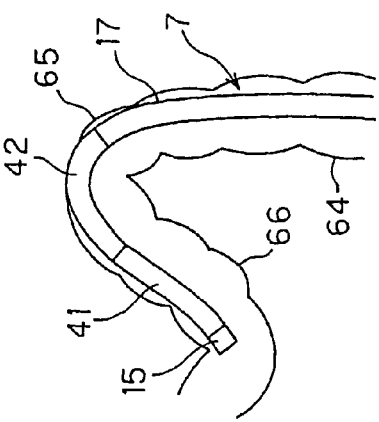
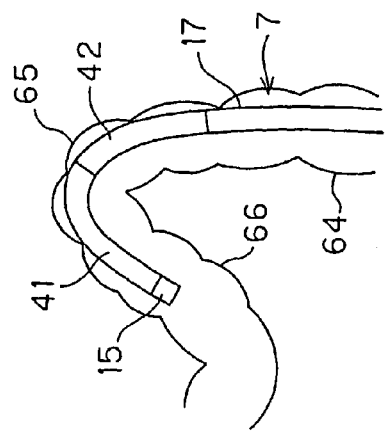

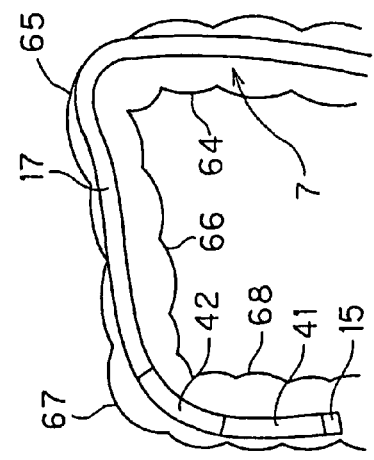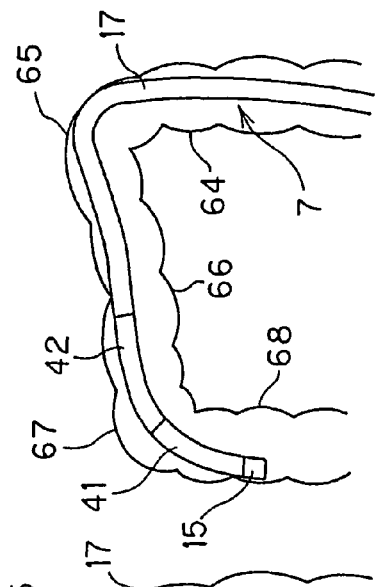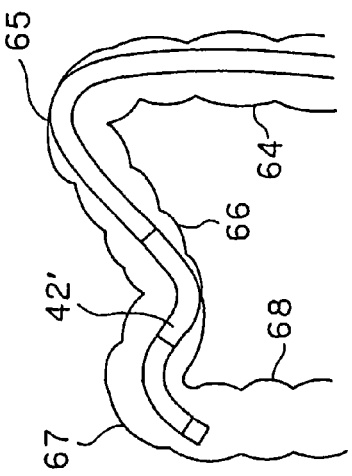

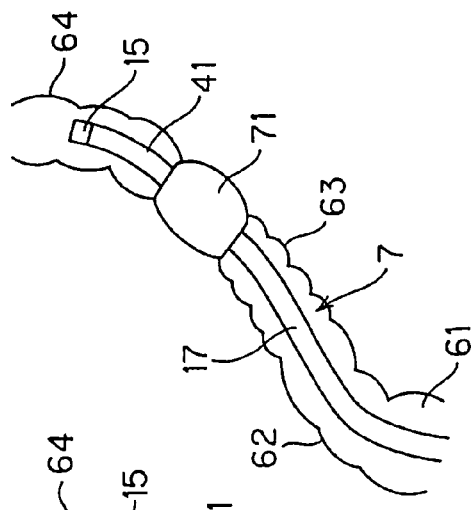
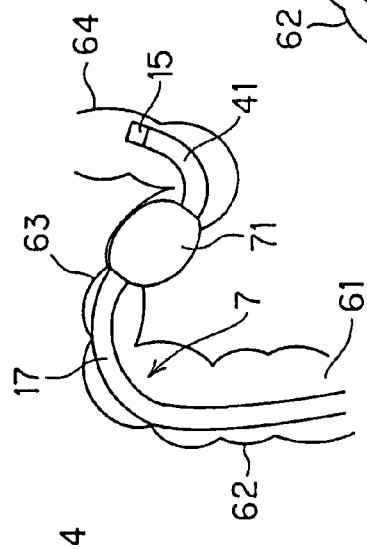
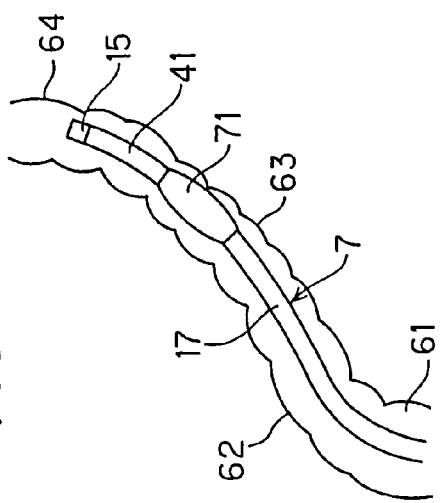

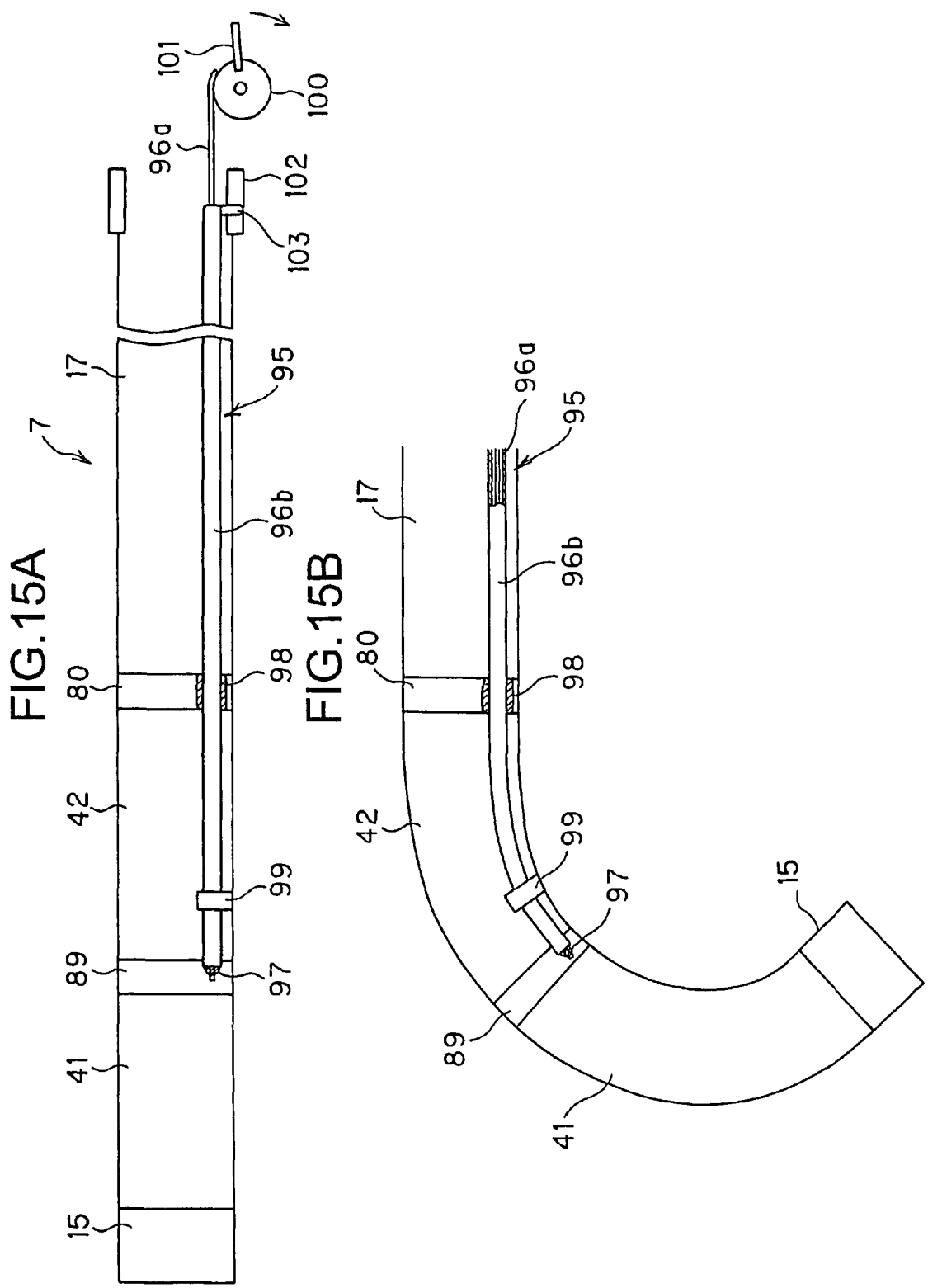

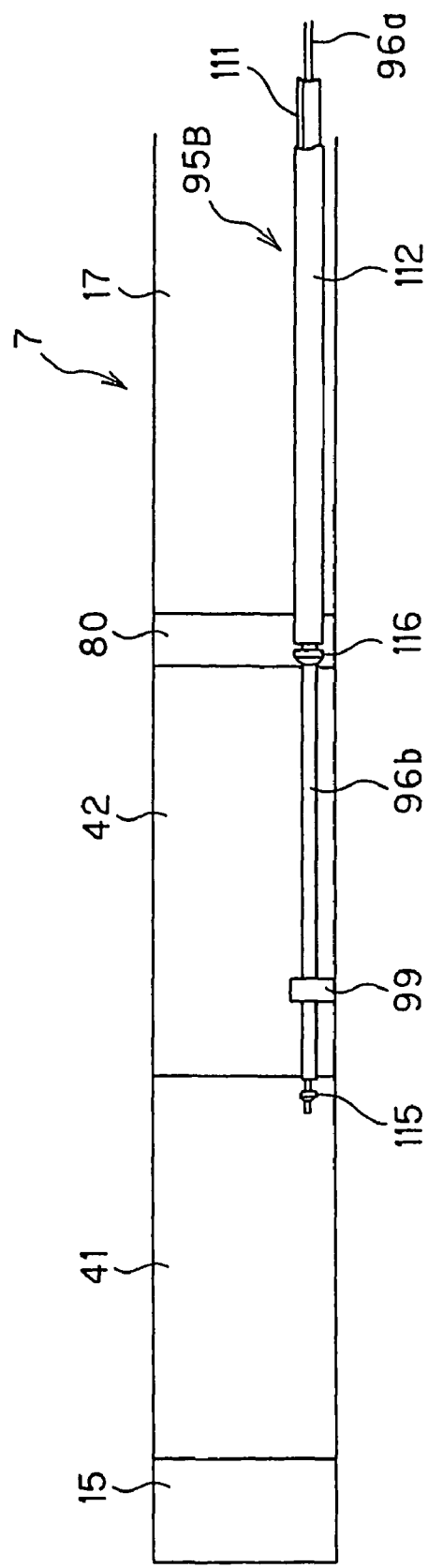

ENDOSCOPE AND METHOD FOR INSERTING ENDOSCOPE INTO COLON

This application claims benefit of Japanese Application No. 2005-240288 filed on Aug. 22, 2005, the contents of which are incorporated by this reference.

BACKGROUND OF THE INVENTION

1. Field of the Invention

The present invention relates to an endoscope having an insertion portion provided with a first and a second bendable sections and a method for inserting the endoscope into a colon.

2. Description of the Related Art

An endoscope in the medical field can be used by inserting an elongated insertion portion into a body cavity for observation of organs and the like in the body cavity or performing various treatments using a treatment instrument inserted into a treatment instrument insertion channel as necessary. In this endoscope insertion portion, a tip end (constituting) portion, a bendable section and a flexible tube portion in order from the tip end are disposed.

When the insertion portion of the endoscope is to be inserted into a body cavity, an operator grips the flexible tube portion and operates an operation knob disposed at an operation portion of the endoscope by a predetermined amount so as to bend the bendable section in a desired direction while pushing it into the body cavity. This type of insertion portion of the endoscope has various improvements to reinforce insertion ability into a curved body cavity.

For example, in the insertion portion of the endoscope described in Japanese Utility Model Publication No. 1-22641, a first bendable section which can be actively operated from outside to be bent in four directions and a second bendable section which is provided with a stay coil and a joint ring and is very easily bent and in a structure passively bent in four directions are provided consecutively in order from the tip end side.

Also, Japanese Unexamined Patent Application Publication No. 2002-143084 discloses an endoscope provided with a first bendable section and a second bendable section with hardness larger than that of the first bendable section.

SUMMARY OF THE INVENTION

The present invention is an endoscope having an insertion portion in which a first bendable section and a second bendable section are sequentially provided at the tip end side of a flexible tube portion, comprising hardness varying means for varying hardness of at least the second bendable section.

By making the hardness of the second bendable section variable with the above construction, insertion and the like into a curved body cavity can be performed more smoothly.

BRIEF DESCRIPTION OF THE DRAWINGS

FIGS. 6A to 6E are explanatory views of an action according to the first embodiment;

FIGS. 7A to 7D are explanatory views of an action of insertion into the depth side of a transverse colon;

FIGS. 9A to 9D are explanatory views of an action by the second embodiment;

FIGS. 15A and 15B are views sowing an outline construction of the tip end side of the insertion portion of the endoscope of a fourth embodiment of the present invention;

FIGS. 16A and 16B are views showing an outline construction and the like of the tip end side of the insertion portion of the endoscope of a first variation of the fourth embodiment.

DETAILED DESCRIPTION OF THE PREFERRED EMBODIMENTS

Respective embodiments of the present invention will be described below referring to the attached drawings.

First Embodiment

Figure 1:
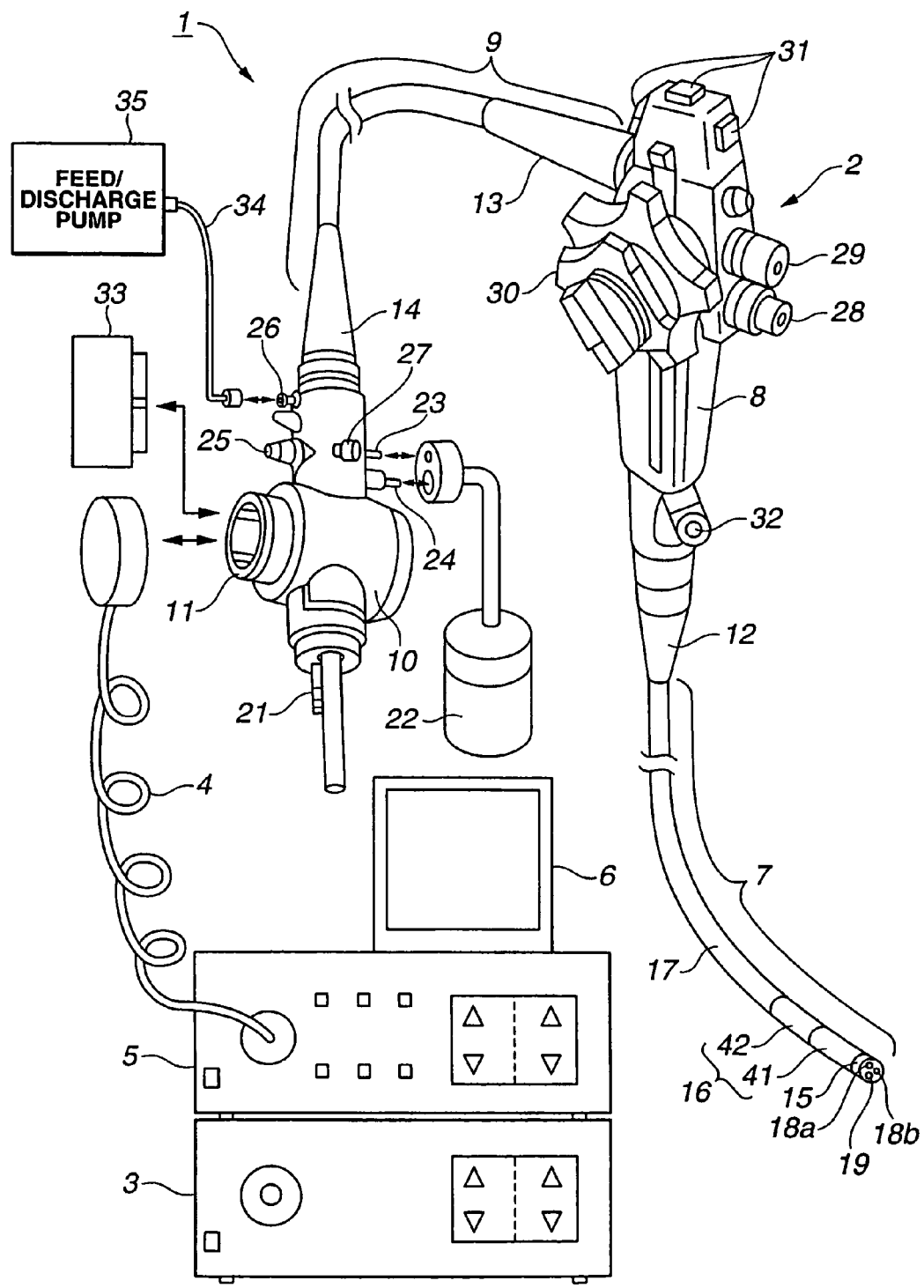
FIG. 1 is an entire construction diagram of an endoscope device provided with an endoscope of a first embodiment of the present invention.
Figure 2:
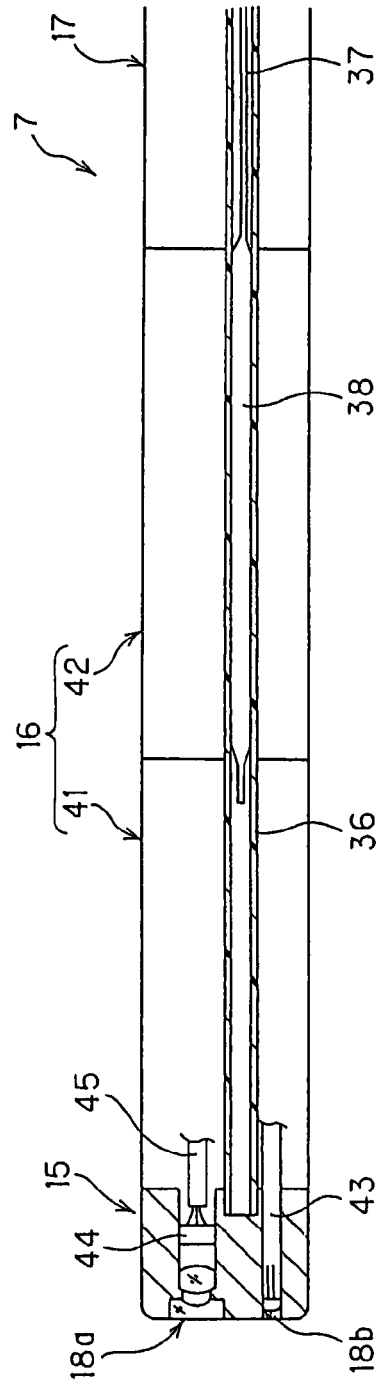
FIG. 2 is a view showing an outline construction of the tip end side of an insertion portion of the endoscope.
Figure 4:
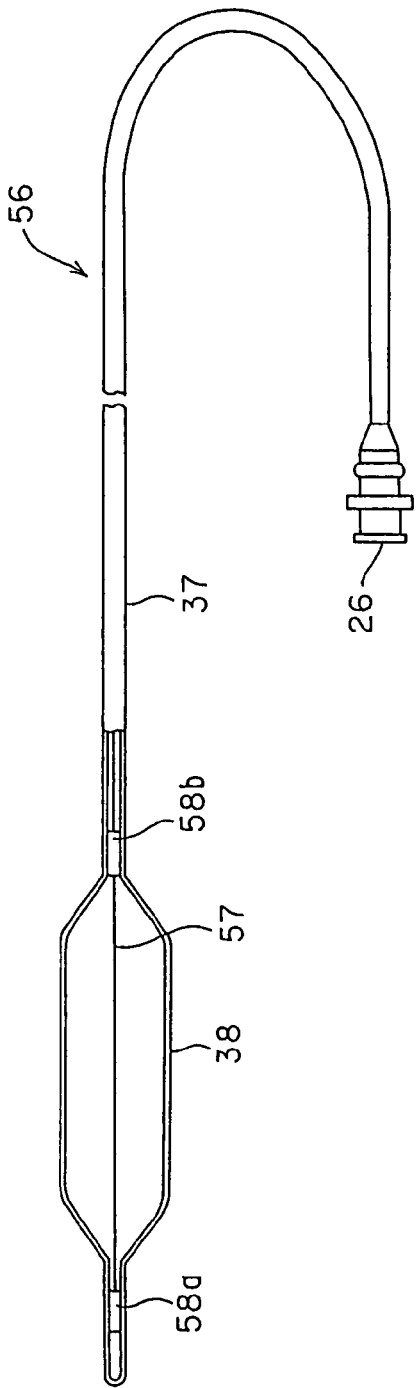
FIG. 4 is a view showing a construction of a balloon catheter portion with variable hardness built in the endoscope.
Figure 3:
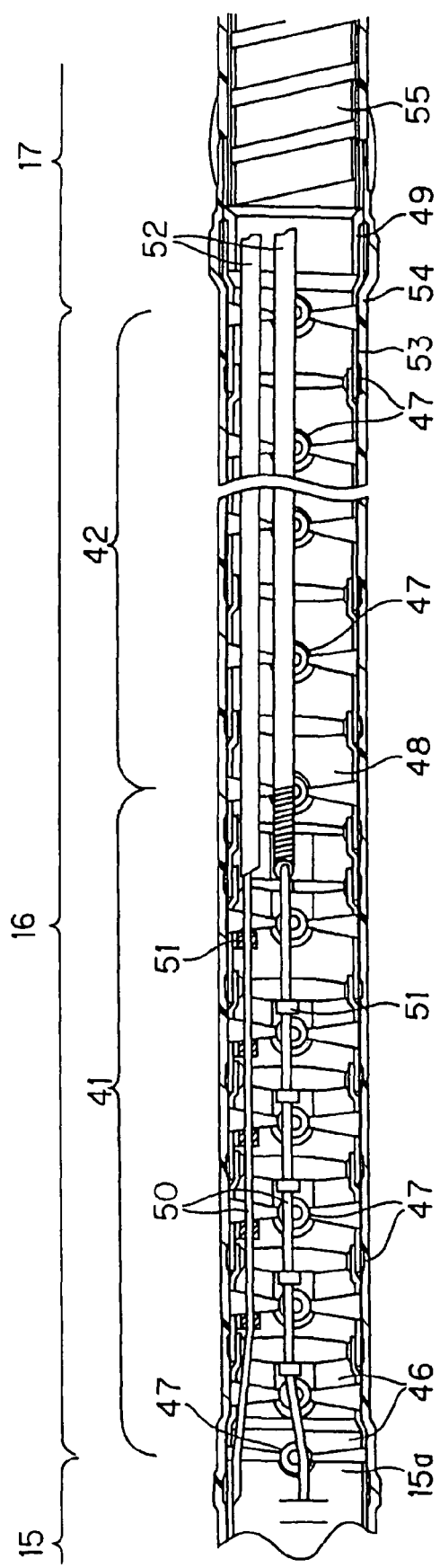
FIG. 3 is a longitudinal sectional view showing an internal construction of the bendable section.
Figure 5:
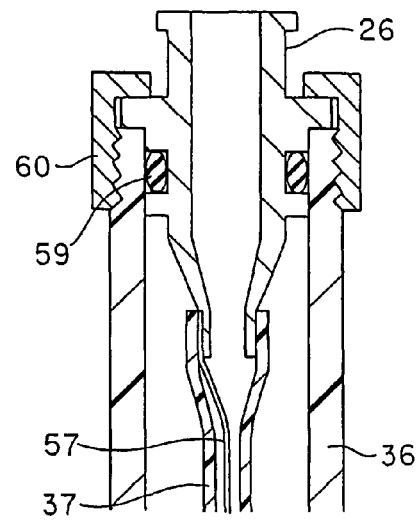
FIG. 5 is a sectional view showing a structure of a fixed portion on the base end side of the balloon catheter.

FIGS. 1 to 7 relate to a first embodiment of the present invention, in which FIG. 1 shows an entire construction of an endoscope device provided with an endoscope of the first embodiment of the present invention, FIG. 2 shows an outline construction of the tip end side of an insertion portion of the endoscope, FIG. 3 shows an internal construction of a bendable section, FIG. 4 shows a construction of a balloon catheter portion with variable hardness built in the endoscope, FIG. 5 shows a structure of a fixed portion on the base end side of the balloon catheter, and FIGS. 6A to 6E and FIGS. 7A to 7D are explanatory views of an action according to this embodiment.

As shown in FIG. 1, an endoscope device 1 comprises, for example, an endoscope 2 provided with an image pickup device, a light source device for supplying illumination light to a light guide detachably connected to the endoscope 2 and provided at the endoscope 2, a video processor 5 connected to the endoscope 2 through a signal cable 4 for controlling the image pickup device of the endoscope 2 and for processing a signal obtained from the image pickup device, and a monitor 6 for displaying an image corresponding to a captured subject image outputted from the video processor 5. The endoscope 2 comprises a component such as an outer sheath having resistance against high-temperature and high-pressure steam so that sterilization processing with the high-temperature and high-pressure steam is possible after being washed when it is used for observation or treatment.

The endoscope 2 comprises an elongated insertion portion 7 having flexibility which can be inserted into a subject (more specifically, into a body cavity), an operation portion 8 connected to the base end side of the insertion portion 7, a universal cord 9 extending from the side portion of the operation portion 8 as a connection cord having flexibility, a connector portion 10 detachably connected to the light source device 3 provided at the end portion of the universal cord 9 and an electric connector portion 11 provided on the side portion of the connector portion 10, to which the signal cable 4 connected to the video processor 5 can be detachably connected.

At a connection portion between the insertion portion 7 and the operation portion 8, an insertion-portion bending prevention member 12 having an elastic member to prevent sharp bending of the connection portion is provided, a similar operation-portion bending prevention member 13 is provided at a connection portion between the operation portion 8 and the universal cord 9, and a similar connector-portion bending prevention member 14 is provided at a connection portion between the universal cord 9 and the connector portion 10.

The insertion portion 7 comprises a flexible tube portion 17 having flexibility, a bendable section 16 which is provided at the tip end side of the flexible tube portion 17 and can be bent by operation of the operation portion 8, and a rigid tip end portion 15 which is provided at the tip end side of the bendable section 16 and at which an observation optical system 18a, an illumination optical system 18b, etc. are disposed.

In this embodiment, the bendable section 16 comprises a first bendable section 41 provided adjacent to the tip end portion 15 and a second bendable section 42 consecutively provided at the rear end of this first bendable section 41, which will be described in FIG. 3.

Moreover, at the tip end portion 15, a water/air supply nozzle for injecting a washing fluid or gas toward an optical member on the outer surface of the observation optical system 18a, and a suction port 19 which is an opening at the tip end side of a treatment instrument channel for inserting the treatment instrument disposed at the insertion portion 7 or sucking the fluid in the body cavity are provided. Also, at this tip end portion 15, a liquid supply port, not shown, is provided, being opened toward an observation subject, for injecting a liquid.

At the connector portion 10, a gas supply base 21 detachably connected to a gas supply source, not shown, incorporated in the light source device 3, a water supply tank pressurizing base 23 and a liquid supply base 24 detachably connected to a water supply tank 22, which is a liquid supply source.

Moreover, a suction base 25 connected to a suction source, not shown, is provided for sucking through the suction port 19. Also, at this connector portion 10, a base 26 is provided, and this base 26 is connected to a feed/discharge pump 35 for feeding/discharging a fluid through a tube 34 for connection.

This base 26 communicates with a tube 37 through which a fluid flows and forms hardness varying means inserted into a tube 36 (See FIG. 2) to be inserted into the insertion portion 7 through the universal cord 9 and the operation portion 8 therein, as will be described later.

And by supplying a fluid from the feed/discharge pump 35, a balloon 38 at the tip end of the tube 37 is inflated, whereby the hardness of the second bendable section 42 in which this balloon 38 is accommodated is increased, that is, the hardness of the second bendable section 42 can be varied by feeding/discharging the fluid to/from the balloon 38. This embodiment is constituted so that, in a state where the fluid is not supplied to the balloon 38, the hardness of the second bendable section 42 is small (low), and by inflating the balloon 38 by supply of the fluid, the hardness of the second bendable section 42 is increased so that the hardness becomes large (high).

It is to be noted that supply and discharge of the fluid by the feed/discharge pump 35 can be carried out by a foot switch or the like, not shown.

Moreover, at the connector portion 10 shown in FIG. 1, an earth terminal base 27 for returning a leakage current to a high-frequency treatment device if a high-frequency leakage current is generated in an endoscope during a high-frequency treatment or the like.

At the operation portion 8 are provided a water/gas feed operation button 28 for operating air/water feed, a suction operation button 29 for operating suction, a bending operation knob 30 for bending operation of the bendable section 16, a plurality of remote switches 31 for remote control of the video processor 5, and a treatment instrument insertion port 32, which is an opening in communication with the treatment instrument insertion channel.

To the electric connector portion 11 of the endoscope 2, a water-proof cap 33 with pressure control valve can be detachably connected. The water-proof cap 33 with pressure control valve is provided with a pressure control valve, not shown.

FIG. 2 shows an outline construction of the tip end side of the insertion portion 7 of the endoscope 2. At the tip end portion 15, the observation optical system 18a (objective optical system) and the illumination optical system 18b are provided adjacently to each other.

A tip end face of a light guide 43 is arranged on the inner side of this illumination optical system 18b so that illumination light supplied from the light source device 3 is transmitted by this light guide 43 and outputted to the front from the tip end face further through the illumination optical system 18b to illuminate a subject such as an affected part.

Also, at an image forming position of the observation optical system 18a, a charge-coupled device (abbreviated as CCD) 44, for example, is arranged as a solid image pickup device so as to form an optical image of the illuminated subject on the CCD 44. And an image signal photoelectrically converted by the CCD 44 is transmitted to the video processor 5 through the a signal cable 45 and the like, converted to a video signal by a signal processing circuit inside the video processor 5, this video signal being outputted to the monitor 6 and the subject image is displayed as an endoscopic image on a display surface of the monitor 6.

At the rear end of the tip end portion 15 shown in FIG. 2, the bendable section 16 comprising the first bendable section 41 and a second bendable section 42 as shown in FIG. 3 is provided.

Also, in this embodiment, the tube 36 with flexibility is inserted into the insertion portion 7 as shown in FIG. 2, and the tip end of this tube 36 is fixed in the state blocked by the tip end portion 15. And into this tube 36, the tube 37 having flexibility and provided with the balloon 38 at the tip end is inserted. In this case, the balloon 38 is provided so as to be located inside the second bendable section 42.

The tube 36 and the tube 37 go from the rear end of the insertion portion 7 through the operation portion 8 and the universal cord 9 to the connector portion 10.

As shown in FIG. 3, a bending piece 46 constituting the first bendable section 41 is connected to the rear end of a tip-end piece 15a fixed to the tip end portion 15 by a rivet 47, and the bending piece 46 in the next stage is rotatably connected to the rear end of this bending piece 46 by the rivet 47 so that a large number of bending pieces 46 are connected capable of being bent in the vertical and the horizontal directions.

Moreover, to the bending piece 46 at the rear end of the first bendable section 41, a bending piece 48 constituting the second bendable section 42 is connected, and the bending piece 48 in the next stage is rotatably connected to the rear end of this bending piece 48 by the rivet 47 so that a large number of bending pieces 48 are connected capable of being bent in the vertical and the horizontal directions.

Moreover, the bending piece 48 at the rear end of the second bendable section 42 is connected to the flexible tube portion 17 through a connecting member 49. The rivets 47 are provided at respective positions corresponding to the vertical and the horizontal directions.

Moreover, wires 50 for bending operation are inserted along the vertical and horizontal directions in the insertion portion 7, and each of the wires 50 is inserted while its position is restricted through an annular wire guide 51 provided on the inner circumferential surface of the bending piece 46 in the first bendable section 41.

Also, each of the wires 50 is inserted into a coil pipe 52 in the second bendable section 42 and after.

And the rear end side of the wire is locked by a sprocket (or a pulley) constituting a bending driving mechanism in the operation portion 8, and by rotationally operating the bending operation knob 30, the wire 50 is pulled and causes the first bendable section 41 to be bent in a desired direction.

The second bendable section 42 is passively bent in accordance with the bent state of the portion into which it is inserted. That is, in the bendable section 16 with the structure shown in FIG. 3, the first bendable section 41 is an active bendable section, while the second bendable section 42 acts as a passive bendable section.

In an example in FIG. 3, the similar bending pieces 46, 48 are employed so that the radius of curvature of the first bendable section 41 when it is bent to the maximum is substantially the same as the radius of curvature of the second bendable section 42 when it is bent to the maximum. This embodiment is not limited to this case, but different values may be set to the radius of curvature at the maximum bending between the tip end side and the rear end side in the first bendable section 41.

Similarly, different values may be set to the radius of curvature at the maximum bending between the tip end side and the rear end side in the second bendable section 42.

Moreover, when the different values are set to the radius of curvature at the maximum bending between the tip end sides and the rear end sides in the first bendable section 41 and the second bendable section 42, substantially the same value may be set to the radius of curvature at the maximum bending at the tip end sides in the first bendable section 41 and the second bendable section 42, for example, and also, substantially the same value may be set to the radius of curvature at the maximum bending at the rear end sides in the first bendable section 41 and the second bendable section 42.

As shown in FIG. 3, the outer circumferential surfaces of the bending pieces 46, 48 in the first bendable section 41 and the second bendable section 42 are covered by a mesh tube 53 and an outer sheath 54 with flexibility. Also, the flexible tube portion 17 has a mesh tube and a flex tube 55 provided inside the outer sheath. It is to be noted that the tube 36 and the like shown in FIG. 2 are not shown in FIG. 3.

In the tube 36 arranged in the insertion portion 7 and the like shown in FIG. 2, a balloon tube 56 with the balloon 38 formed integrally in connection at the tip end of the tube 37 is inserted (accommodated).

In this balloon tube 56, a guide wire 57 is inserted within the tube 37 and the balloon 38 with rich expansion/contraction property provided at its tip end and capable of inflation and contraction.

The guide wire 57 is fixed by a fixing member 58a at the tip end side of the balloon 38 and also fixed by a fixing member 58b provided with a hollow portion in the vicinity of the rear end of the balloon 38. As for the structure of the rear end (base end) of the tube 37, it is fixed to the base 26 as shown in FIG. 5 and connected to the feed/discharge pump 35 through the tube 34 shown in FIG. 1.

As shown in FIG. 5, the rear end of the tube 37 is fixed to the base 26 for connection, and the rear end of the tube 36 through which the tube 37 is inserted is fitted at the outer circumferential surface of this base 26.

In this case, a clearance between the outer circumference surface on the base side and the tube 36 is made into the water-tight structure by an O-ring 59 engaged in a circumferential groove provided on the outer circumferential surface of the base 26 and further fixed by fastening the tube 36 by a fastening ring 60 such as a nut onto the outer circumferential surface of the base 26.

The endoscope 2 with such a construction in this embodiment, having the bendable section 16 in which the first bendable section 41 capable of being bent is provided at the tip end side of the insertion portion 7 and the second bendable section 42 which is bent easily is provided at the rear end of this first bendable section 41, characterized in that the balloon 38 is inflated/contracted by feeding/discharging a fluid so that hardness of the second bendable section 42 can be variably controlled. And when the insertion portion 7 is to be inserted into a curved portion in a body cavity as will be described below, insertion work can be performed smoothly by variably controlling the hardness of the second bendable section 42.

Action according to this embodiment in the above construction will be described below referring to FIGS. 6A to 6E.

A case of colon examination by inserting the insertion portion 7 of the endoscope 2 of this embodiment from an anus 61 will be described.

As shown in FIG. 6A, the tip end side 15 of the insertion portion 7 is inserted from the anus 61 through a rectum 62 to a descending colon 64 side at the depth of a sigmoid colon 63 curved in the S-shape.

When the tip end portion 15 reaches the descending colon 64, by pulling the base-end side of the insertion portion 7 while twisting the insertion portion 7, the sigmoid colon portion can be made linear along the shape of the insertion portion 7 close to a straight line as shown in FIG. 6C.

Before this linear forming operation, by turning ON a fluid supply switch of a foot switch, not shown, a fluid is supplied into the balloon 38, which inflates the balloon 38 with the liquid, and the hardness of the second bendable section 42 is increased with elasticity.

After the hardness of the second bendable section 42 is set larger in this way, by twisting and pulling the insertion portion 7 at the base-end side of the insertion portion 7, the state can be brought from that in FIG. 6A to that in FIG. 6C.

In the conventional example of the above-mentioned Japanese Utility Model Publication No. 1-22641, in this operation of linear forming operation, since the hardness of the second bendable section 42 is low, a state as shown in FIG. 6B is brought about, which incurs a possibility that the insertion portion 7 might pull out.

By performing pushing operation at the base-end side of the insertion portion 7 after straightening operation as shown in FIG. 6C, the tip end portion 15 can be further inserted to the depth side, and by pushing it while largely bending the first bendable section 41 in the vicinity of a splenic flexure portion 65, the tip end portion 15 side can be inserted into a transverse colon 66 as shown in FIG. 6D.

When further pushing the tip end portion 15 into the depth side of the transverse colon 66, a fluid discharge switch of the foot switch is turned ON, for example, so as to reduce the amount of the fluid in the balloon 38 and to lower the hardness of the second bendable section 42 so that a large hardness becomes an appropriate hardness, and the base-end side of the insertion portion 7 is pushed in.

Since the hardness of the second bendable section 42 is lowered, the second bendable section 42 can be smoothly moved to the depth side while being bent along a bent inner surface of the splenic flexure portion 65 as shown in FIG. 6E with the pushing operation.

In this case, as with the conventional example of the above-mentioned Japanese Unexamined Patent Application Publication No. 2002-143084, if the hardness remains high, a large external force is required to bend the second bendable section, and if the pushing operation is performed in this state, the second bendable section will push the bending inner surface of the splenic flexure portion 65, which might make smooth insertion difficult. On the other hand, in this embodiment, the hardness is made smaller (lower) so as to facilitate smooth insertion.

Also, by performing the pushing operation after increasing the hardness of the second bendable section 42 in the inserted state as in FIG. 6E, the tip end portion 15 can be smoothly inserted to the depth side of the transverse colon 66.

How to insert the insertion portion to the depth side from FIG. 6E will be further described using FIGS. 7A to 7D. In the state of insertion as in FIG. 6E, by increasing the hardness of the second bendable section 42 and pushing it in, the second bendable section 42 is brought into the substantially straight state as shown in FIG. 7A and it can be inserted to the depth side of the transverse colon 66.

On the other hand, in the conventional example of the above-mentioned Japanese Utility Model Publication No. 1-22641, a second bendable section 42' which is easy to be bent is affected by the curved shape of the transverse colon 66 and is bent in an unintended direction as shown in FIG. 7D, and even if the operation to push in the insertion portion is performed at the base-end side, the tip end portion is hard to be advanced to the depth side, which is a problem.

In this embodiment, in the state shown in FIG. 7A, by pushing in the insertion portion 7 while the first bendable section 41 is bent in the state where the hardness of the second bendable section 42 is increased, it is possible to pass the first bendable section 41 through a hepatic flexure portion 67 as shown in FIG. 7B to advance it to an ascending colon 68 side.

Moreover, in the state where the hardness of the second bendable section 42 is lowered, by pushing in the insertion portion 7 at the base-end side, the tip end portion 15 can be inserted to the depth side of the ascending colon 68 without the second bendable section 42 acting as resistance at the hepatic flexure portion 67 as shown in FIG. 7C.

That is, in this embodiment, after passing the splenic flexure portion 65, by increasing the hardness of the second bendable section 42 to suppress bending of the second bendable section 42 so that the insertion operation at the base-end side can be smoothly transmitted to the tip end portion 15, and the insertion portion 7 can be smoothly inserted to the depth side.

According to this embodiment in this way, since the hardness of the second bendable section 42 can be varied, the insertion work and the like of the insertion portion 7 into the depth side within a colon can be performed more smoothly than the conventional example.

It is to be noted that in the above description, a case of insertion into a colon was explained, but according to the endoscope 2 of this embodiment, insertion to a curved portion in a body cavity can be carried out smoothly.

As a variation of the first embodiment, the balloon tube 56 shown in FIG. 4 may be inserted into a treatment instrument channel and used while the balloon 38 portion at its tip end is fixed to the inside of the second bendable section 42.

In this case, the base 26 is protruded from the treatment instrument insertion port 32 and connected to the feed/discharge pump 35 through the tube 34. And it may be so constituted that, by operation of the foot switch, not shown, similarly to the first embodiment, the fluid is fed/discharged to/from the balloon 38 to vary the hardness of the second bendable section 42.

And when it is inserted to a target portion in a body cavity, if treatment by another treatment instrument is desired, the balloon tube 56 may be pulled out of the treatment instrument channel so that treatment by another treatment instrument can be carried out. This variation has a merit that application to an existing endoscope is possible.

Second Embodiment

Figure 8:
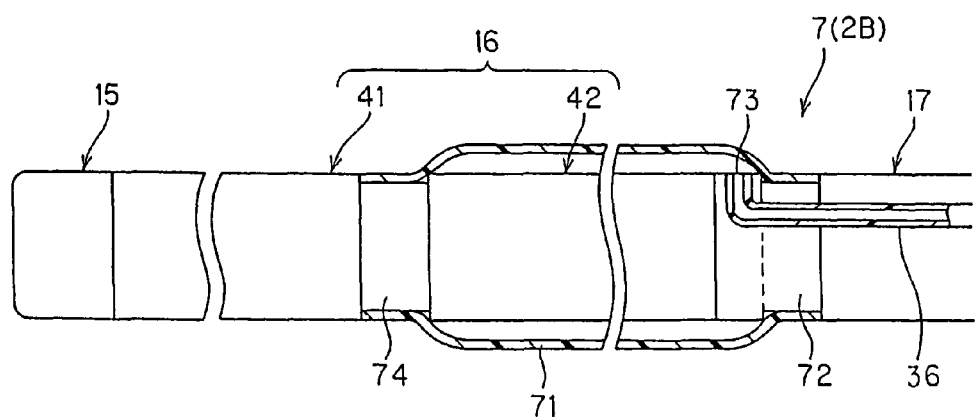
FIG. 8 is a view showing an outline construction of the tip end side of the insertion portion of the endoscope of a second embodiment of the present invention.

Next, a second embodiment of the present invention will be described referring to FIG. 8 and FIGS. 9A to 9D. FIG. 8 shows a construction of the tip end side of the insertion portion 7 in an endoscope 2B of the second embodiment.

The first embodiment has a construction that the balloon 38 is arranged inside the second bendable section 42, but this embodiment has a construction that a balloon 71 is provided on an outer surface of the second bendable section 42.

Specifically, the tip end side of the tube 36 arranged in the insertion portion 7, which was described in the first embodiment, is an opening end 73 opened at the outer surface at a position of a connection portion 72 at the boundary between the tip end of the flexible tube portion 17 and the second bendable section 42.

Moreover, the outer circumferential surface of the second bendable section 42 is covered by the balloon 71. This balloon 71 is in the substantially circular tube shape and its rear end is fixed to the outer circumferential surface of the connection portion 72 by an adhesive or the like, while its front end is fixed at a connection portion 74 at the boundary between the first bendable section 41 and the second bendable section 42. And the structure is made water tight or air tight so that a fluid supplied to this balloon 71 does not leak to the outside of the balloon 71.

A thin portion with a thickness of about that of the balloon 71 is formed on the outer circumferential surfaces of the connection portions 72 and 74 where the rear end and the front end of the balloon 71 are fixed, and by fixing the rear end and the front end of the balloon 71, respectively, the smoothly connected outer surface is formed without a step.

Moreover, the rear end of the tube 36 is connected to the base 26 at the connector portion 10, and this base 26 is connected to the feed/discharge pump 35 through the tube 34 as described in the first embodiment. In this embodiment, the rear end of the tube 36 is connected to the base 26 while the tube 37 is not connected to the base 26.

And by operating the foot switch, not shown, as in the first embodiment, the fluid can be fed/discharged by operating the feed/discharge pump 35. By feeding/discharging the fluid, the balloon 71 can be inflated or contracted, and as in the first embodiment, the hardness of the second bendable section 42 can be varied while maintaining elasticity.

Since the balloon 71 is provided on the outer circumferential surface of the second bendable section 42 in this embodiment, when the hardness is increased, the point where the outer circumferential surface of the second bendable section 42 is inflated by the balloon 71 is different from that in the first embodiment. And in this embodiment, when the balloon 71 is inflated, the outer circumferential surface of the balloon 71 is brought into close contact with the inner wall of the body cavity on the outer circumference side of the balloon 71 so that the second bendable section 42 on which this balloon 71 is provided can be locked (fixed) by the inner wall by frictional force.

Action of this embodiment with the above construction will be described referring to FIGS. 9A to 9D.

Similarly to the first embodiment, the insertion portion 7 is inserted from the anus 61 as shown in FIG. 9A and the tip end portion 15 is inserted through the colon 62 and to the descending colon 64 side at the depth of the sigmoid colon 63 curved in the S-shape.

After that, a fluid such as a liquid or a gas is supplied to the balloon 71 to inflate the balloon 71 as shown in FIG. 9B, and by bringing this inflated balloon 71 into close contact in a wide area with the intestinal wall, this balloon 71 portion can be locked (fixed) by the intestinal wall.

After that, an operator can, by performing pulling operation of the base-end side of the insertion portion 7, prevent pulling-out of the insertion portion 7 by the balloon 71 provided on the outer circumferential surface of the second bendable section 42 while being inflated and locked by the intestinal wall and reduce the length of the sigmoid colon 63 as shown in FIG. 9C.

After reduction as in FIG. 9C, the liquid supplied to the balloon 71 is discharged and the balloon 71 is contracted as shown in FIG. 9D so that the insertion portion 7 can be further inserted to the depth by the pushing-in operation.

According to this embodiment, insertion to a curved portion within a body cavity can be carried out more smoothly as in the first embodiment.

Also, by inflating the balloon 71, the second bendable section 42 provided with the balloon 71 can be locked in the body cavity, by which the insertion work can be carried out more smoothly.

Third Embodiment

Next, a third embodiment of the present invention will be described referring to FIGS. 10A and 10B. The third embodiment is constituted so that the hardness of the second bendable section can be varied by moving means inserted into the insertion portion in the axial direction of the insertion portion.

Figure 10A:
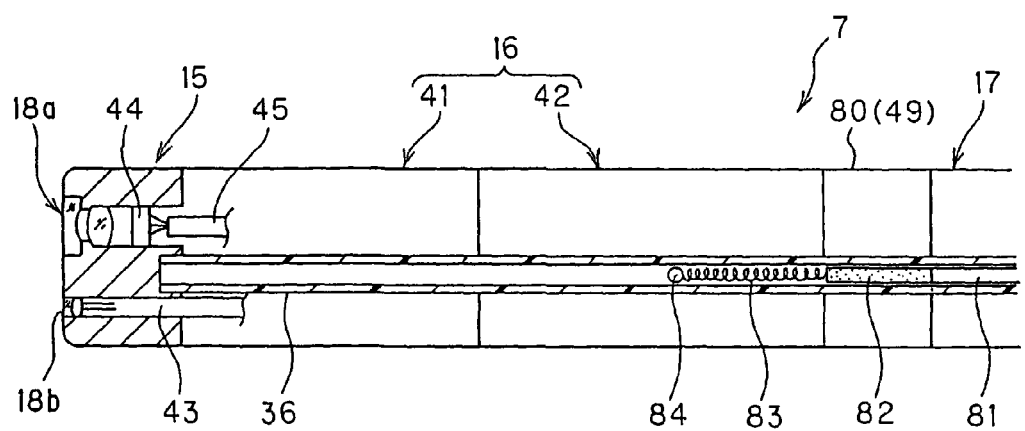
FIGS. 10A and 10B are views showing an outline construction of the tip end side of the insertion portion of the endoscope of a third embodiment of the present invention.

FIG. 10A shows an outline construction of the tip end side of the insertion portion of the endoscope in the third embodiment.

As in the first embodiment, the flexible tube 36 is provided in the longitudinal direction in the insertion portion 7, and in this tube 36, a stylet 81 as a lengthy member with flexibility is inserted capable of sliding through the tube 36.

In the vicinity of the tip end of this stylet 81, a rigid portion 82 is provided, and at the tip end of this rigid portion 82, a roughly coiled coil portion 83 is provided. Moreover, at the tip end of this coil portion 83, a spherical tip-end tip 84, for example, is provided to enable smooth movement.

This stylet 81 is formed by a member with rich flexibility, specifically, a closely coiled coil or the like, and the rigid portion 82 provided at the tip end of this stylet 81 is set to have the same length as that of a rigid connection portion 80 provided at the boundary portion between the rear end of the second bendable section 42 and the tip end of the flexible tube portion 17. This rigid connection portion 80 corresponds to the connecting member 49 in the first embodiment.

Also, the coil portion 83 is slightly more rigid than the stylet 81, for example, in this embodiment. The rigid portion 82 has hardness higher than the stylet 81 and the coil portion 83.

The rear end of this stylet 81 extends from the tube 36 to the outside in the vicinity of the operation portion, for example, so that operation to move the position of the rigid portion 82 to the second bendable section 42 side by pushing in the rear end or the like.

Action of this embodiment with the above construction will be described. In the state shown in FIG. 10A, the coil portion 83 is arranged in the second bendable section 42, and its hardness is relatively low. Also, the rigid portion 82 provided at the stylet 81 is arranged at the position of the rigid connection portion 80, and this rigid portion 82 can remain in the state where the hardness in the vicinity of the boundary between the rear end of the second bendable section 42 and the flexible tube portion 17 is not affected.

Figure 10B:
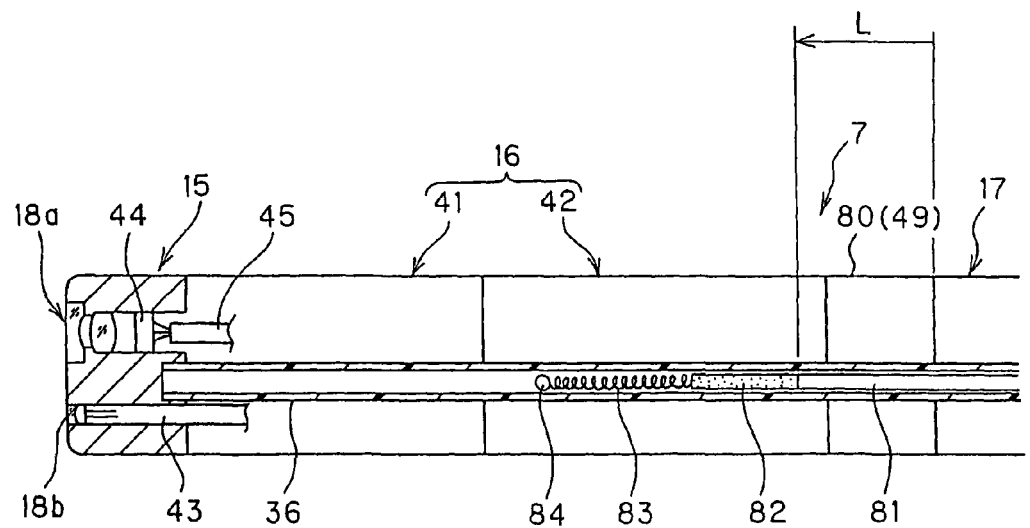

In the state in FIG. 10A, by advancing the position of the rigid portion 82 to the second bendable section 42 side by a distance longer than the length for the connection portion 80 (in the axial direction), a distance L, for example, the state shown in FIG. 10B is brought about.

In the state shown in FIG. 10B, the rigid portion 82 with high hardness is arranged inside the second bendable section 42, which can make the hardness of the second bendable section 42 large.

According to this embodiment in this way, since the hardness of the second bendable section 42 is made variable, smooth insertion can be performed as described in the first embodiment even if it is inserted to the depth side of a colon and the like.

By retreating the position of the rigid portion 82 to the flexible tube portion 17 side in the state in FIG. 10A, the hardness of the second bendable section 42 can be further lowered (in this case, the hardness of the vicinity of the tip end of the flexible tube portion 17 is increased by the rigid portion 82). The rear end of the stylet 81 is connected to a lever, not shown, provided at the operation portion, and advance/retreat may be effected by operating the lever.

In this embodiment, the tube 36 with the slidable stylet 81 is provided in the insertion portion 7, but the same working effect is also exerted by inserting the stylet 81 in the channel for insertion of a treatment instrument. Alternatively, the stylet 81 may be slidably inserted into a pipeline for forward water supply. Alternatively, the stylet 81 may be built in the endoscope or made separate (detachable).

Figure 11:
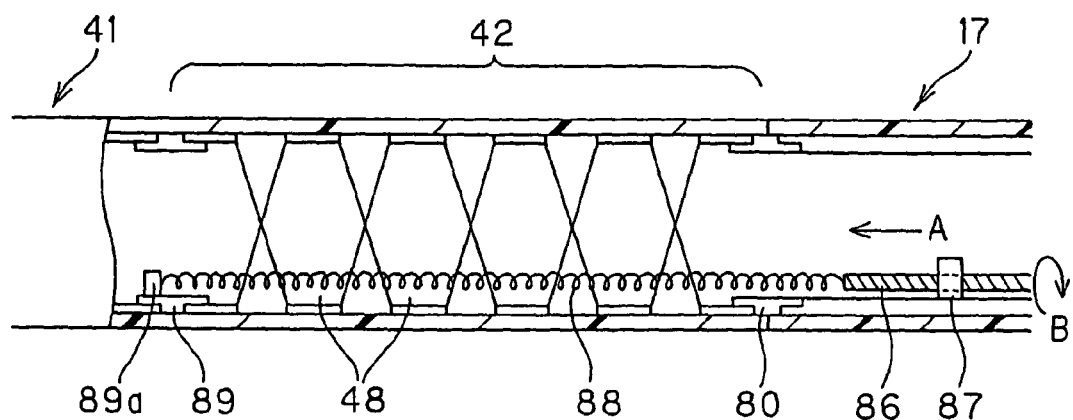
FIG. 11 is a view showing an outline construction of the tip end side of the insertion portion of in a first variation of the third embodiment.

Next, a first variation of this embodiment will be described referring to FIGS. 11 and 12. FIG. 11 shows an outline construction to vary the hardness in the vicinity of the second bendable section 42.

In the flexible tube 17, a thin and flexible torque tube 86 with a high function to transmit a torque is arranged along an inner wall surface through a tube receiver 87 provided with a hole through which this torque tube 86 is passed.

At the tip end of this torque tube 86, the rear end of a roughly coiled helical coil spring 88 is mounted, and the tip end of this coil spring 88 is fixed to a fixed portion 89a provided at a rigid connection portion 89 at the boundary between the rear end of the first bendable section 41 and the tip end of the second bendable section 42. In FIGS. 11 and 12 (also in FIGS. 13 and 14, which will be described later), the bending piece 48 and the like in the second bendable section 42 are shown in a simplified way.

The above coil spring 88 is in the flexible state in FIG. 11, that is, with a low hardness, and has a characteristic that the hardness is increased when it is compressed or set in the more closely coiled state.

Moreover, this coil spring 88 is arranged so as to cover the entire length of the second bendable section 42 in its inside, for example.

The above torque tube 86 comprises a coil in a three-layered structure, for example, with different coiling directions, and the tube with the hardness rarely changed is employed in whichever direction it is rotated.

The rear end side of this torque tube 86 extends to the operation portion, and the torque tube 86 can be advanced/retreated or rotated by operation of a lever, rotating knob, etc., not shown, provided at the operation portion. And the hardness of the roughly coiled coil spring 88 is made variable by the advance/retreat or rotation.

Action of this variation with the above construction will be described.

Figure 12:
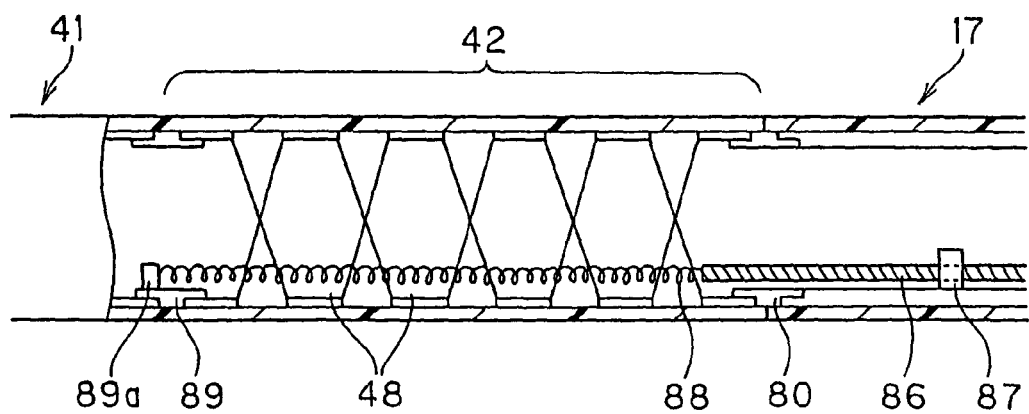
FIG. 12 is a view showing an outline of a state where the hardness is set so that it becomes larger than that in the state in FIG. 11.

In the state where the hardness of the second bendable section 42 is low as shown in FIG. 11, for example, if the hardness of this second bendable section 42 is to be increased, a user presses the torque tube 86 at the operation portion side to move the torque tube 86 to a forward direction A so as to reduce the coil spring 88 connected to its tip end as shown in FIG. 12.

When the roughly coiled coil spring 88 is reduced in this way, this coil spring 88 becomes difficult to be bent, and the hardness of the second bendable section 42 can be increased.

Alternatively, it may be so constituted that, not by moving the torque tube 86 but by rotating it in a coiling direction B of the coil spring 88, the coiling pitch of this coil spring 88 is made narrow (small), and as a result, the coil spring 88 is made more difficult to be bent so that the hardness of the second bendable section 42 can be increased.

According to this variation, the hardness of substantially only the second bendable section 42 can be varied by a simple operation of push and pull or rotation of the torque tube 86, which can realize favorable manipulability. Also, since it is only necessary to insert only the thin and roughly coiled coil spring 88 and the torque tube 88 into the insertion portion, the diameter of the insertion portion can be kept small.

In the above first variation, description was made that the hardness is varied by moving the torque tube 86, but when the hardness is to be varied by contracting the coil spring 88 by this movement, the construction is not limited to the torque tube 86 but it may be formed by a lengthy member having flexibility.

Figure 13A:
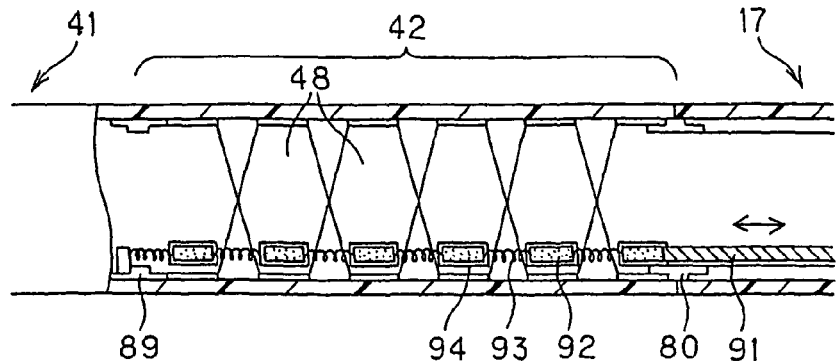
FIGS. 13A and 13B are views showing an outline construction and the like of the tip end side of the insertion portion in a second variation of the third embodiment.
Figure 13B:
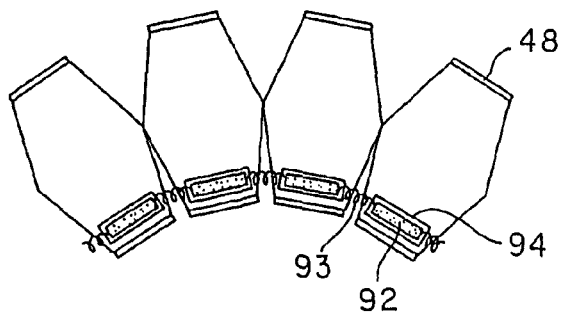

Next, a second variation of this embodiment will be described referring to FIGS. 13A to 14B. FIG. 13A shows an outline construction to vary hardness in the vicinity of the second bendable section 42 in the second variation.

In the flexible tube portion 17, a closely coiled coil 91 having flexibility, for example, is inserted. At the tip end of this closely coiled coil 91, a rigid portion 92 and a roughly coiled coil 93 with hardness lower than that of the rigid portion 92 are connected alternately.

In the first state where the hardness of the second bendable section 42 is lowered, that is, in the state shown in FIG. 13A, the rigid portion 92 is arranged in a guide tube 94 mounted to the bending piece 48, and the length (in the longitudinal direction) of this rigid portion 92 is set so that it is accommodated within the length (in the longitudinal direction) of the bending piece 48.

And the rigid portion 92 arranged inside each of the bending pieces 48 is connected with each other by the roughly coiled coil 93. In this case, when the second bendable section 42 is bent by an external force, the roughly coiled coil 93 is compressed and bent as shown in FIG. 13B, and the second bendable section 42 is easy to be bent, that is, in the state with low hardness.

On the other hand, if the hardness of the second bendable section 42 is to be increased, operation to move the closely coiled coil 91 is performed by pulling or pushing forward the rear end of the closely coiled coil 91. The closely coiled coil 91 is pulled, for example, to bring it from the first state shown in FIG. 13A to the second state shown in FIG. 14A.

Figure 14A:
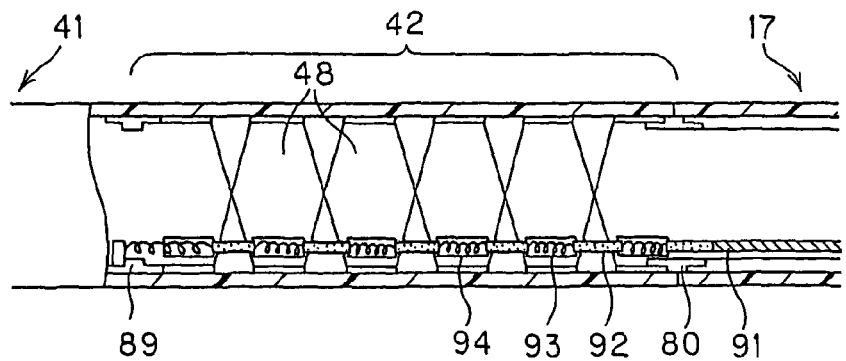
FIGS. 14A and 14B are views showing an outline of a state where the hardness is set so that it becomes larger than that in the state in FIG. 13A.
Figure 14B:
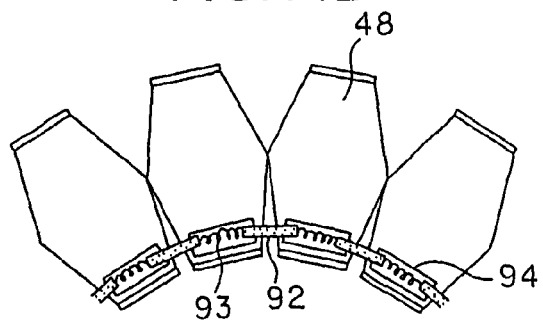

In the second state shown in FIG. 14A, the rigid portion 92 is arranged between the adjacent bending pieces 48. When an external force acts on the second bendable section 42 to bend it in this second state, the rigid portion 92 hits the guide tube 94 and becomes a resistance to prevent bending, which makes bending difficult. That is, the hardness is increased in this second state.

By the moving operation of the closely coiled coil 91 to set a middle state between the first state shown in FIG. 13A and the second state shown in FIG. 14A, an intermediate value between both hardness values in FIG. 13A and FIG. 14A can be set.

According to this variation, it has an effect that, by moving the closely coiled coil 91 by a short moving stroke amount, the hardness of the second bendable section 42 can be largely varied.

That is, the hardness can be varied from the low hardness state to the maximum hardness state with a movement amount of about ½ of the length in the axial direction of the bending piece 48 constituting the second bendable section 42. The same effects as those in the third embodiment are also exerted.

Fourth Embodiment

Next, a fourth embodiment of the present invention will be described referring to FIGS. 15A and 15B. FIG. 15A shows an outline construction of the tip end side of the insertion portion of the endoscope in the fourth embodiment.

In this embodiment, a hardness varying member 95 is inserted in the insertion portion 7. This hardness varying member 95 comprises a hardness varying wire 96*a* and a closely coiled coil 96*b* into which this hardness varying wire 96*a* is inserted.

The tip ends of the hardness varying wire 96*a* and the closely coiled coil 96*b* constituting this hardness varying member 95 extend to the vicinity of the boundary between the first bendable section 41 and the second bendable section 42, for example. And the both tip ends are made as a fixed portion 97 fixed by solder or the like.

The closely coiled coil 96*b* in the hardness varying member 95 is made as a fixed portion 98 fixed to the connection portion 80 at the boundary between the second bendable section 42 and the flexible tube portion 17 by solder or the like.

And the tip end portion of this hardness varying member 95 is a free end, and by pulling the rear end of the hardness varying wire 96*a*, the entire hardness varying wire 96*a* is moved in the longitudinal direction. At that time, the tip end of this hardness varying wire 96*a* presses and compresses backward the middle portion between the fixed portion 97 and the fixed portion 98 of the closely coiled coil 96b arranged in the second bendable section 42 so that the hardness of this closely coiled coil 96b in the second bendable section 42 can be increased.

A guide member 99 is provided in the second bendable section 42 for restricting movement of the hardness varying member 95 in the direction crossing the longitudinal direction when the second bendable section 42 and the like is bent as shown in FIG. 15B.

Also, the rear end of the hardness varying wire 96a is fixed to a rotatable pulley 100 in the operation portion, and by performing a rotating operation of a lever 101 mounted to this pulley 100 in a direction shown by an arrow, the hardness varying wire 96a is pulled so as to vary the hardness of the hardness varying member 95 in the second bendable section 42.

Moreover, the rear end of the closely coiled coil 96b is also connected to a cam ring 102 provided at the operation portion. At the rear end of the closely coiled coil 96b, a pin 103 is projected, for example, and this pin 103 is engaged in a cam groove of the cam ring 102.

And by rotating this cam ring 102, a user can move the rear end of the closely coiled coil 96b to the front along the longitudinal direction, and by applying a compression force to the closely coiled coil 96b arranged in the flexible tube portion 17 from its rear end side to the middle portion between the cam ring 102 and the fixed portion 98, the hardness can be varied so that the low hardness state when no force is applied is changed to the large hardness.

According to this embodiment with the above construction, the hardness of the second bendable section 42 can be varied by operation of the lever 101, and by further performing rotating operation of the cam ring 101 independently of hardness varying of the second bendable section 42, the hardness of the flexible tube portion 17 can be also varied.

Therefore, when the insertion portion 7 is to be inserted to the depth side of a colon, for example, the hardness of the flexible tube portion 17 can be also varied and more smooth insertion can be achieved.

Specifically, as described in FIGS. 6A to 6E, smooth insertion into the depth side of a colon can be carried out by varying the hardness of the second bendable section 42.

Moreover, when the hardness of the second bendable section 42 is increased from the state shown in FIG. 6E as described in FIGS. 7A to 7C and the tip end side of the insertion portion 7 is inserted into the depth side of the transverse colon 66, more smooth and easy insertion can be realized.

That is, such description was made that smooth insertion can be achieved if the hardness of the second bendable section 42 is increased, when the tip end side of the insertion portion 7 is inserted to the depth side of the transverse colon 66 from the state shown in FIG. 6E as shown in FIG. 7A.

In this case, if the hardness of the flexible tube portion 17 is also increased, a force to push at the base-end side of the insertion portion 7 is transmitted to the tip end portion 15 side of the insertion portion 7 more efficiently by suppressing bending of the flexible tube portion 17.

Therefore, the insertion work of the insertion portion 7 can be carried out more smoothly and easily by further varying the hardness of the flexible tube portion 17 rather than the insertion work by varying the harness of the second bendable section 42 as in the first embodiment. In the case of insertion from FIG. 7A to FIG. 7C, the insertion work can be carried out more smoothly and easily in the same way.

Next, a first variation of this embodiment will be described referring to FIGS. 16A and 16B. FIG. 19A shows an outline construction at the tip end side of the insertion portion 7 in the first variation. FIG. 16B shows a construction of a hardness varying member 95B in this variation.

In this variation, a second wire 111 is fixed to an outer circumferential surface of the closely coiled coil 96b constituting the hardness varying member 95 shown in FIG. 15A, and the closely coiled coil 96b with this second wire 111 fixed is inserted into a second closely coiled coil 112 to form the hardness varying member 95B of this variation.

In the hardness varying member 95B in this variation, at the tip end of the hardness varying wire 96a, a first stopper 115 is mounted for applying a compression force to this closely coiled coil 96b from the tip end side by restricting movement of the closely coiled coil 96b.

And by pulling this hardness varying wire 96a backward, the first stopper 115 presses the tip end of the closely coiled coil 96b arranged on its outside to the rear side. This pressing applies a compression force to the closely coiled coil 96b inside the second bendable section 42 so as to increase the hardness.

Moreover, also on the outer circumferential surface of the closely coiled coil 96b arranged in the vicinity of the connection portion 80 at the boundary between the second bendable section 42 and the flexible tube portion 17, a second stopper 116 is provided for applying a compression force to the second closely coiled coil 112 from the tip end side by restricting movement of the second closely coiled coil 112.

And by pulling the second wire 111 backward, the second stopper 116 presses the tip end of the closely coiled coil 112 arranged on its outside to the rear side. This pressing compresses the second closely coiled coil 112, which increases its hardness.

In this variation with the above construction, if the hardness of the second bendable section 42 is desired to be increased, the hardness varying wire 96a is pulled backward. Then, the first stopper 115 is moved backward, and at that time, and the closely coiled coil 96b portion from the vicinity of the tip end of the second bendable section 42 to the vicinity of rear end of the second bendable section 42, where the second stopper 116 is provided, that is, the closely coiled coil 96b portion arranged inside the second bendable section 42 is compressed and its hardness can be increased.

Also, by pulling the rear end of the second wire 111 backward so that a compression force is applied by the second stopper 116 to the second closely coiled coil 112, its hardness can be increased. That is, the hardness of the second closely coiled coil 112 arranged in the flexible tube portion 17 can be increased.

In this variation in this way, the hardness of the second bendable section 42 can be varied as in the fourth embodiment, and the hardness of the flexible tube portion 17 can be also varied independently.

As a simplified construction in this variation, a portion to pull the second wire 111 may not be provided. And it may be so constituted that, by pulling the hardness varying wire 96a, the closely coiled coil 96b in the second bendable section 42 is compressed so as to increase its hardness, and by further pulling the wire, the second closely coiled coil 112 is compressed so as to increase the hardness of the flexible tube portion 17.

Figure 17:
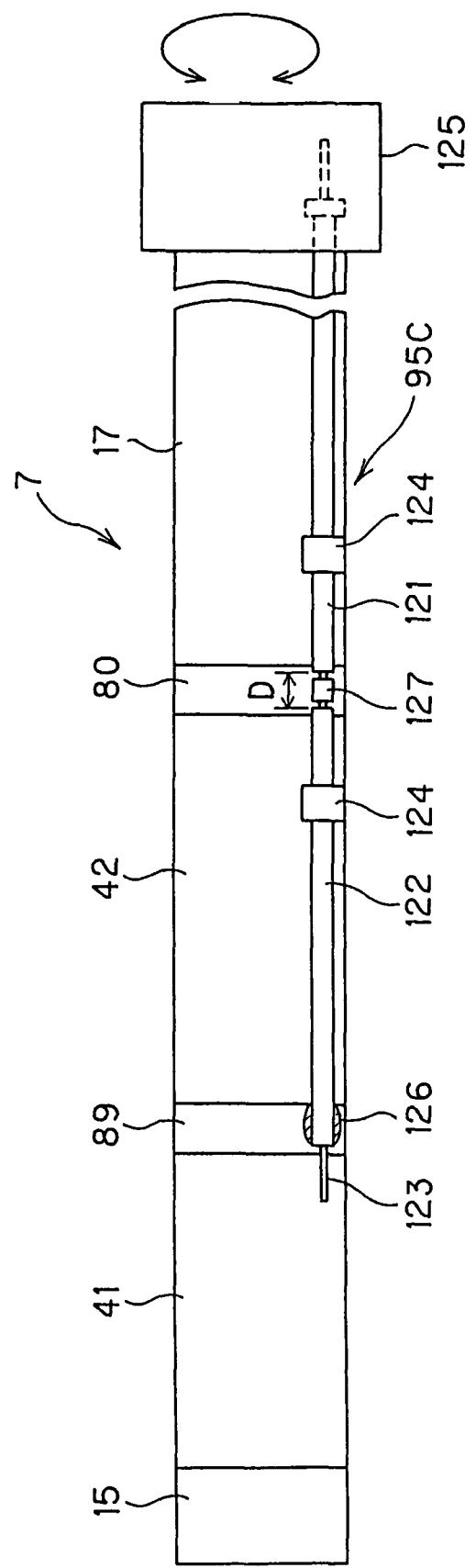
FIG. 17 is a view showing an outline construction of the insertion portion of a second variation of the fourth embodiment.

Next, a second variation of this embodiment will be described referring to FIG. 17. FIG. 17 shows a construction of the tip end side of the insertion portion 7 provided with a hardness varying member 96C of the second variation.

In this variation, a first closely coiled coil 121 is inserted in the flexible tube portion 17 and a second closely coiled coil 122 is inserted in the second bendable section 42, into both of which a common wire 123 is inserted, and they are arranged in the longitudinal direction of the insertion portion 7, with the circumferential positions restricted by a guide tube 124.

Also, the position of the rear end of the first closely coiled coil 121 is restricted by a stopper in the operation portion, and the wire 123 extending from the rear end of the first closely coiled coil 121 is connected to a wire operation knob 125 through a connection mechanism, not shown, and by rotationally moving this wire operation knob 125, the wire 123 can be advanced/retreated.

Moreover, the tip end of the second closely coiled coil 122 is made as a fixed portion 126 fixed at the connection portion 89 between the first bendable section 41 and the second bendable section 42 by solder or the like.

Moreover, the tip end of the first closely coiled coil 121 and the rear end of the second closely coiled coil 122 are opposed and separated by a distance D, for example, at the connection portion 80 between the second bendable section 42 and the flexible tube portion 17, and a stopper 127 is fixed to the wire 123 between the both.

This stopper 127 is fixed to the wire 123 by the length shorter than the distance D. And a user can, by rotating the wire operation knob 125, move the wire 123 forward or backward in the rotating direction. When it is advanced, for example, a compression force is made to act by the stopper 127 to the second closely coiled coil 122 so as to compress this second closely coiled coil 122, and the hardness of the second bendable section 42 can be increased.

Alternatively, when the wire 123 is moved backward, a compression force is made to act by the stopper 127 to the first closely coiled coil 121 so as to compress the first closely coiled coil 121, and the hardness of the flexible tube portion 17 can be increased.

According to this variation, the hardness of the second bendable section 42 and the flexible tube portion 17 can be selectively varied by changing the rotating direction of the wire operation knob 125 as common hardness operating means.

In the second variation in FIG. 17, it may be so constituted that, at the base-end side, a stopper at the rear end of the first closely coiled coil 121 (for restricting a position in its longitudinal direction) is mounted to an operating member made movable by a rotation operation such as the wire operation knob 125, and a compression force is made to act to the first closely coiled coil 121 by operating this operating member so that the hardness is made variable. In this case, the hardness of the second bendable section 42 and the flexible tube portion 17 can be varied substantially independently by the operation of the wire operation knob 125.

Embodiments and the like constituted by partially combining the above respective embodiments also belong to the present invention.

Also, in the above respective embodiments, a construction of a passive bendable section which is bent in the bending direction of the first bendable section 41 is described as the second bendable section 42, but it may be such a construction that the second bendable section 42 can be actively bent.

As mentioned above, according to the present invention, an operator can carry out work of insertion into a curved body cavity and the like smoothly. That is, when an insertion portion provided with the first bendable section and the second bendable section is to be inserted to a curved portion such as a colon, the operator can perform smooth insertion by varying the hardness of the second bendable section.

What is claimed is:

1. A method for inserting an endoscope into a colon, the endoscope comprising:

an insertion portion having a tip end side portion and a rear end side portion, the insertion portion comprising:
a flexible tube portion provided at the rear end side portion of the insertion portion,
a first bendable section selectively bent in a bending direction operated by a bending direction operation section, the first bendable section being provided at the tip end side portion of the insertion portion and formed by rotatably connecting a plurality of bending pieces along a longitudinal direction of the insertion portion,
a second bendable section provided between the flexible tube portion and the first bendable section, and formed by rotatably connecting a plurality of bending pieces along the longitudinal direction of the insertion portion, and
hardness varying means for varying the hardness of the second bendable section relative to the hardness of the flexible tube portion and the first bendable section, the hardness varying means including:
a balloon tube having at a tip end thereof an inflatable balloon, and
a tube into which the balloon tube is inserted such that the balloon is located within a range where the second bendable section is provided, the tube being provided in the longitudinal direction of the insertion portion, and a tip end of the tube being fixed, in a closed state, to the tip end side portion of the insertion portion, and
a base fixing section provided in a vicinity of a base end of the endoscope, and detachably connected to a fluid supply device for supplying a fluid, the base fixing section fixing a rear end of the balloon tube in an open state inside a rear end of the tube,
the method comprising steps of:
causing the first bendable section to reach a descending colon;
increasing the hardness of only the second bendable section relative to the hardness of the flexible tube portion and the first bendable section by supplying the fluid from the fluid supply device to the balloon; and
making a sigmoid colon portion straight by twisting and pulling the insertion portion after the hardness of only the second bendable section is increased and inserting the insertion portion into the colon.

2. The method according to claim 1, further comprising a step of
pushing in the insertion portion while bending the first bendable section in the vicinity of a splenic flexure portion.

3. The method according to claim 2, further comprising a step of
decreasing the hardness of the hardness varying means and pushing in the insertion portion when the insertion portion is to be inserted into the depth of a transverse colon.

4. The method according to claim 3, further comprising a step of
increasing the hardness of the hardness varying means and pushing in the insertion portion when the insertion portion is to be further inserted into the further depth of a transverse colon.

5. The method according to claim 4, further comprising a step of
increasing the hardness of the hardness varying means and pushing in the insertion portion in the vicinity of a hepatic flexure portion.

6. The method according to claim 5, further comprising a step of
   decreasing the hardness of the hardness varying means and pushing in the insertion portion when the insertion portion is inserted into the depth of the ascending/descending colon.

7. The method according to claim 1, wherein the tube and the balloon tube are inserted through the insertion portion, the operation portion at the rear end of the insertion portion, and a universal cord extended from the operation portion, and the base fixing section located at the rear ends of the tube and of the balloon tube is provided in a connector provided at an end portion of the universal cord.

* * * * *